United States Patent
Tastard et al.

(10) Patent No.: US 8,857,240 B2
(45) Date of Patent: Oct. 14, 2014

(54) LIQUID-DISSOLVED GAS CHARACTERIZATION FACILITY AND METHOD

(75) Inventors: Christophe Tastard, Plougoumelen (FR); Philippe Gleize, Bussy Saint Georges (FR); Alain Toquet, Nanterre (FR)

(73) Assignee: GFD SUEZ, Courbevoie (FR)

( * ) Notice: Subject to any disclaimer, the term of this patent is extended or adjusted under 35 U.S.C. 154(b) by 694 days.

(21) Appl. No.: 13/090,325

(22) Filed: Apr. 20, 2011

(65) Prior Publication Data

US 2011/0259466 A1    Oct. 27, 2011

(30) Foreign Application Priority Data

Apr. 22, 2010 (FR) ...................................... 10 53064

(51) Int. Cl.
| | |
|---|---|
| G01N 7/00 | (2006.01) |
| G01N 1/10 | (2006.01) |
| B01D 19/00 | (2006.01) |
| G01N 1/22 | (2006.01) |
| G01N 1/40 | (2006.01) |

(52) U.S. Cl.
   CPC .............. B01D 19/0036 (2013.01); G01N 1/10 (2013.01); G01N 1/4022 (2013.01); G01N 2001/105 (2013.01); G01N 1/2294 (2013.01)
   USPC .............................. 73/19.01; 73/19.1; 141/94

(58) Field of Classification Search
   USPC ................................... 73/19.01, 19.1; 141/94
   See application file for complete search history.

(56) References Cited

U.S. PATENT DOCUMENTS

| | | | |
|---|---|---|---|
| 4,202,216 A | | 5/1980 | Bull et al. |
| 4,217,782 A | | 8/1980 | Pont |
| 4,302,976 A | | 12/1981 | Bull |
| 4,566,332 A | | 1/1986 | Collingwood |
| 5,313,950 A | | 5/1994 | Ishikawa et al. |
| 5,419,196 A | | 5/1995 | Havira et al. |
| 5,499,531 A | * | 3/1996 | Henderson ................... 73/64.45 |
| 5,569,837 A | * | 10/1996 | Hinaga ......................... 73/19.01 |
| 5,604,297 A | * | 2/1997 | Seiden et al. .................. 73/19.1 |
| 5,653,250 A | * | 8/1997 | Sigmund et al. .................. 137/7 |

FOREIGN PATENT DOCUMENTS

| | | | |
|---|---|---|---|
| EP | 272861 | * | 6/2008 |
| JP | 59-26031 | * | 2/1984 |
| JP | 2007-225439 | * | 9/2007 |

OTHER PUBLICATIONS

Search report for FR 1053064 completed Jan. 17, 2011.*

* cited by examiner

*Primary Examiner* — Daniel S Larkin
(74) *Attorney, Agent, or Firm* — Harness, Dickey & Pierce, PLC

(57) ABSTRACT

The invention particularly relates to a facility for characterizing liquid-dissolved gas.
In its most complete embodiment, this facility comprises a liquid collecting capsule (1) and a circuit of fluid with two branches (2, 3) including a plurality of valves (41-47), the first branch (2) making it possible to retain the liquid, and the second branch (3) making it possible to extract vacuum gases and including in particular a sealed joint section (31), a pumping facility (32), a variable volume enclosure (33), and pressure and temperature measurement means (34-37).

13 Claims, 1 Drawing Sheet

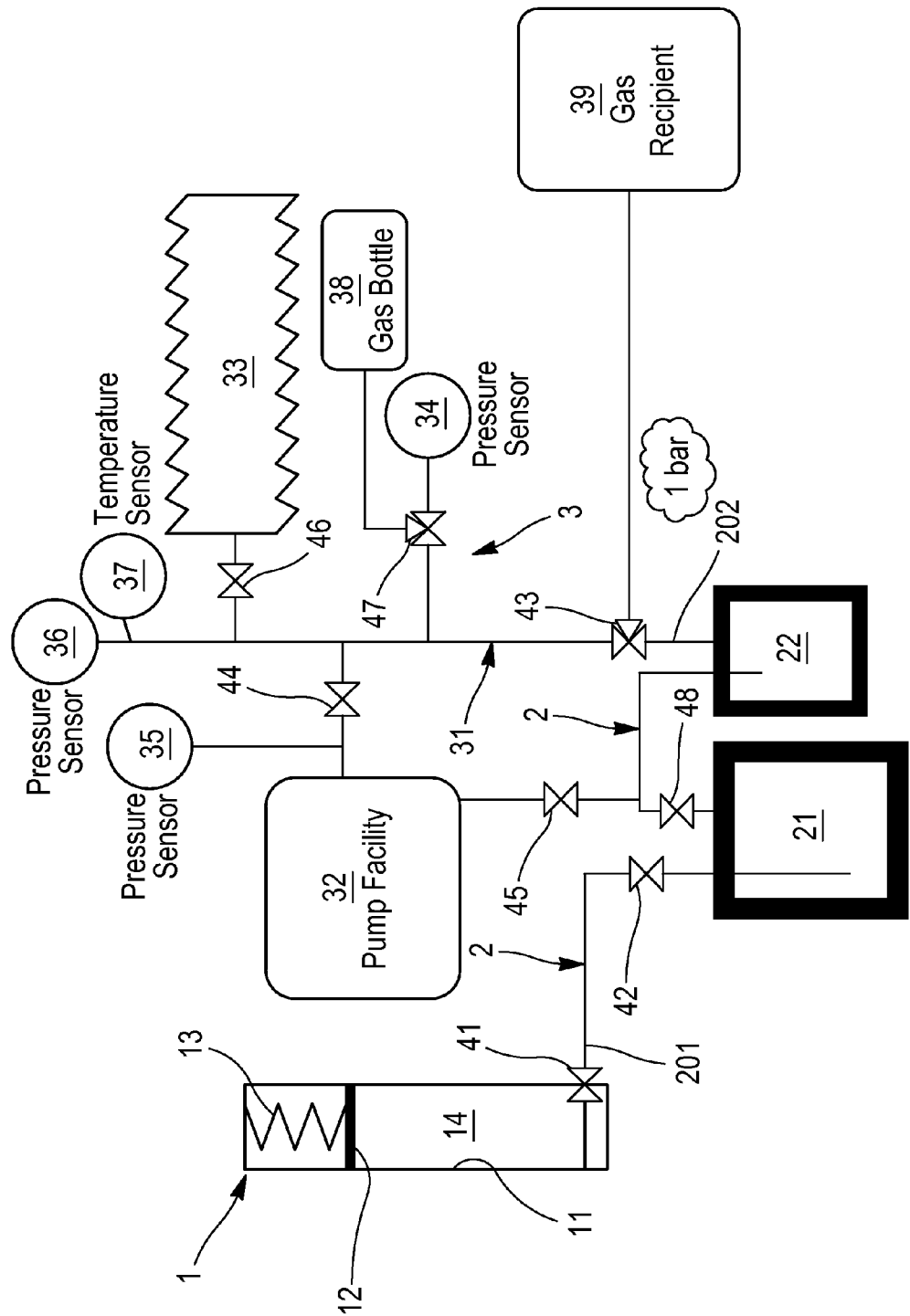

US 8,857,240 B2

LIQUID-DISSOLVED GAS CHARACTERIZATION FACILITY AND METHOD

FIELD

The invention generally relates to the management of energy resources.

BACKGROUND

According to a first aspect, the invention more specifically relates to a liquid-dissolved gas characterization facility, this facility including at least a circuit of fluid including first and second branches, the first branch exhibiting a first end for the intake of the liquid and a second end being connected to the second branch, and each branch including at least a valve.

A facility of this type is for example known from Japanese patent application JP 59 026031.

It is known to store fuel gas to ensure the optimal supply thereof to consumers, including at the time of peaks of consumption or upon a potential failure of a supplier.

To this end, it is also known to store gas in a water table. In this configuration, the gas from deposits and conveyed by the transport network, is injected into a porous rock which contains water. A small part of this natural gas is then dissolved in the water of the aquifer.

During follow-up of the activity of these storages, it is necessary to collect quantitative information on the dissolved gas content in the water of the storage water table.

To this end, water samples are collected at the storage pressure (up to 80 bars at well bottom) and are preserved in titanium capsules.

These capsules are then brought to a laboratory where the dissolved gas is extracted and analyzed.

To optimize this characterization operation, it is advisable to extract all the dissolved gases, to determine their volume, and analyze them.

It is known to proceed with this operation by means of equipment using a mercury pump. The principle is to vacuum the capsule containing the liquid sample, and to flow gas by a mercury stream. The dissolved gas is then recovered in a test-tube to determine the volume thereof, then transferred to an analyzer.

However, these manipulations are very long and constraining, notably, because of the toxicity of mercury used and the complexity of the equipment.

Many techniques were proposed for the characterization of gas dissolved in liquids, in particular, in oil or in sea water.

Examples of these techniques are given in patent documents U.S. Pat. No. 6,602,327, U.S. Pat. No. 4,853,006, US2060242, US20030084916, U.S. Pat. No. 5,645,625, and U.S. Pat. No. 5,183,486.

However, in the majority of these techniques, the gas is extracted, the totality of the dissolved gas volume not being able to be collected and measured.

Although, in certain instances, an estimate of the quantity of dissolved gas can be carried out according to thermodynamic calculations (balance between the gas phase and the liquid phase), techniques for the partial extraction of dissolved gases do not make it possible to determine the exact composition of dissolved gases. Indeed light gases are extracted more easily, which leads to a heavy gas impoverishment of the extracted gas sample. Thus, the extracted gas is not representative of the quality of the gases dissolved in the fluid.

Other techniques, for example described in the patent documents U.S. Pat. No. 3,968,678, U.S. Pat. No. 4,681,601, and U.S. Pat. No. 4,394,635, were proposed to indirectly evaluate the volume of dissolved gases, without carrying out the extraction thereof.

However, these techniques do not make it possible at all to obtain exploitable information relating to the nature of the dissolved gases.

SUMMARY

In this context, the purpose of the present invention is to propose a facility and a process making it possible to at least extract, in a simple and fast manner, gases dissolved in a liquid sample with a reliability such that the nature of dissolved gases can be determined at least in a later step.

To this end, the facility of the invention, which is further in accordance with the generic definition given thereto by the above preamble, is substantially characterized in that the first branch comprises, in series in this order between its first and second ends, a first valve, a first container suitable to collect the liquid, a second valve designed to shut-off or establish a communication between the fluid input and this first container, and a trap designed to trap the liquid vapor, in that the second branch comprises a tight joint section connected to the second end of the first branch, a third valve designed to shut-off or establish a communication between the first connect and the joint section, a pumping facility, a fourth valve designed to shut-off or establish a communication between the joint section and this pumping facility, a fifth valve designed to shut-off or establish a communication between the first branch and this pumping facility, this fifth valve being connected to the first branch between the first container and the vapor trap, a first variable volume enclosure, a sixth valve designed to shut-off or establish a communication between the joint section and this variable volume enclosure, measurement means connected at least selectively to the joint section and including at least a pressure sensor, and a seventh valve allowing the connection between the joint section to said pressure sensor or to a pressurized inert gas bottle.

Moreover, it is judicious that this facility be provided such as to comprise a liquid sampling capsule selectively connected to the first end of the first branch and whose first valve controls the opening, that the first container be temperature-controlled and ultrasound-emitting, and that the measurement means comprise a temperature gauge.

Preferably, this facility further comprises a gas recipient linked to the third valve and composed of a gas analyzer or a second variable volume enclosure for collecting the extracted gas, said third valve being designed to shut-off or establish a communication between the joint section and this recipient.

The pressure measurement means comprise for example at least a pressure sensor suitable to measure pressures at least equal to 1 mbar, and at least a pressure sensor suitable to measure pressures at most equal to 0.001 mbar.

Advantageously, the pumping facility comprises a primary pump and a turbo-molecular pump.

In the preferred embodiment of the invention, the capsule comprises a cylinder, a piston and a spring, the piston delimiting with the cylinder a variable volume sealed room for containing the liquid, and the spring biasing the piston in a direction for reducing the volume of the room.

If the liquid primarily consists of water, the first temperature controlled container can be led to a temperature of 0 Celsius, and the vapor trap comprises for example a second temperature controlled container led to a temperature at most equal to −10 degrees Celsius, and typically of about −20 degrees Celsius.

The invention also relates to a process for characterizing gas dissolved, at a predetermined pressure, within a liquid, this process comprising at least an extracting step, implementing a facility such as previously described, and being characterized in that the extracting step comprises at least the operations of:

(a) collecting, at the predetermined pressure, a liquid sample in the sealed capsule having a known volume;

(b) the first valve of the facility being shut-off, connecting the capsule to the first end of the first branch;

(c) the third valve of the facility being open in the direction of first branch/joint section connection, the seventh valve being open in the direction of joint section/pressure sensor, opening the second, fourth, fifth and sixth valves, and temporarily activating the pumping facility to vacuum the first branch and the joint section of the fluid circuit;

(d) shutting-off the fourth and fifth valves to isolate the pumping facility, and shutting-off the third and seventh valves;

(e) opening the first valve to transfer into the first container the liquid previously contained in the capsule, and shutting-off again the first valve;

(f) waiting for a thermal balance to establish between the first container and the vapor trap, then opening the third valve in the direction of first branch/joint section;

(g) waiting for the balance to establish, then measuring the pressure and the temperature in the joint section and the variable volume enclosure to derive the amount of gas extracted therefrom.

Operation (c) is preferably carried out by vacuuming the fluid circuit with a pressure at most equal to 0.001 mbar.

If the method is carried out in a facility including an extracted gas recipient, such as an analyzer or a second variable volume enclosure for collecting the extracted gas, this process can then be completed by a step itself including the operations of:

(h) shutting-off the third valve;

(i) compressing extracted gas to a predetermined pressure;

(j) vacuuming the gas recipient and the portion of the joint section between this recipient and the third valve; and (k) opening the third valve in the direction of joint section/gas recipient passage and emptying the variable volume enclosure for passing the gas therein towards the gas recipient.

This characterization process can then easily comprise an additional operation (l) of analyzing the gas sent into the gas recipient.

The process of the invention can also comprise at least a reiteration step including itself the operations of:

(m) shutting-off the third valve, opening the fourth, sixth and seventh valves in the joint section/pressure sensor direction and temporarily activating the pumping facility to vacuum the joint section of the fluid circuit;

(n) shutting-off the fourth and seventh valves to isolate the pumping facility from the joint section;

(o) repeating operation (f);

(p) repeating operation (g);

(q) repeating operation (h);

(r) repeating operation (i);

(s) repeating operation (j);

(t) repeating operation (k); and (u) repeating operation (l).

Operation (i) of compressing the extracted gas to a predetermined pressure is advantageously carried out by reducing the volume of the variable volume enclosure and/or opening the seventh valve to communicate the pressurized inert gas bottle with the joint section.

BRIEF DESCRIPTION OF THE DRAWING

Other characteristics and advantages of the invention will become more apparent from the following description thereof given hereafter, which is indicative and by no means restrictive, with reference to the annexed drawing.

FIG. 1 is a diagram of a facility in accordance with the invention.

DETAILED DESCRIPTION

As stated previously, the invention relates to a facility for characterizing gas dissolved in a liquid.

This facility comprises at least a liquid sampling capsule 1 and a fluid circuit substantially formed of a first branch 2 and a second branch 3.

The first branch 2 has an end 201 to be connected to capsule 1, and a second end 202 being connected to the second branch 3.

This first branch 2 comprises, in series in this order between its ends 201 and 202, a first valve 41, a first container 21, a second valve 42, and a second container 22 forming a vapor trap.

The first valve 41 controls the opening of capsule 1, while the second valve 42 is designed to shut-off or establish a communication between capsule 1 and first container 21.

This first container 21, of which function is particularly to collect the liquid contained in capsule 1, is led to a temperature controlled for example around 0 degrees Celsius if this liquid is substantially composed of water.

Preferably, this container 21 is designed to emit ultrasounds and has a volume ranging between 120% and 150% of the volume of capsule 1.

The second container 22, which is designed to trap the vapor of the liquid contained in capsule 1, is led to a temperature lower than −10 degrees Celsius and for example of about −20 degrees Celsius if this liquid is substantially composed of water.

The second branch 3 of the fluid circuit comprises at least a sealed joint section 31, a pumping facility 32, a first variable volume enclosure 33, measurement means 34-37, and at least five additional valves 43 to 47.

The sealed joint section 31 is connected to the second end 202 of the first branch 2 of the fluid circuit, the third valve 43 being precisely designed to shut-off or to establish a communication between this first branch 2 and this joint section 31.

The pumping facility 32 advantageously comprises a primary pump and a turbo-molecular pump.

The fourth valve 44 is designed to shut-off or establish a communication between the joint section 31 and this pumping facility 32.

The fifth valve 45 is designed to shut-off or to establish a communication between the first branch 2 of the fluid circuit and this pumping facility 32.

The variable volume enclosure 33 is comparable to a mechanical bellows making it possible to reduce dead volumes once contracted.

The sixth valve 46 is designed to shut-off or to establish a communication between the joint section 31 of the second branch 3 and this variable volume enclosure 33.

The measurement means 34 to 37 are connected at least selectively to the joint section 31 and include at least a pressure sensor 34 and a temperature gauge 37, the latter being at least designed to measure temperatures between −10 and 30 degrees Celsius.

The seventh valve 47 makes it possible to connect the joint section 31 to the pressure sensor 34 previously mentioned, or to a pressurized inert gas bottle 38.

An eighth valve 48 can be considered between the first container 21 and the second container 22.

The measurement means 34 to 37 comprise for example a pressure sensor 36 for measuring pressures at least equal to 1 mbar, and one or two pressure sensors such as 34 and 35, for measuring pressures at most equal to 0.001 mbar.

Preferably, the facility of the invention further comprises a gas recipient 39 composed of a gas analyzer or a second variable volume enclosure for collecting the extracted gas.

This gas recipient 39 is linked to the third valve 43 which has also a function of shutting-off or establishing a communication between this recipient 39 and the joint section 31 of the second branch 3.

Capsule 1 advantageously comprises a cylinder 11, a piston 12 and one spring 13.

For example, cylinder 11 is made from titanium and is designed to resist high pressures, for example, of about 80 bars.

Piston 12, which is movably mounted in cylinder 11, delimits with this cylinder a sealed variable volume room 14 for containing the liquid sample in which the gases are dissolved.

Lastly, the function of spring 13 is to apply to piston 12 an elastic force in a direction suitable to reduce the volume of room 14.

The method of the invention, which preferably implements a facility such as previously described, comprises, in its most complete form, the operations of:

(a) collecting, at the predetermined pressure, a liquid sample in the sealed capsule 1 having a known volume;
(b) the first valve 41 of the facility being shut-off, connecting capsule 1 to the first end 201 of the first branch 2;
(c) the third valve 43 of the facility being open in the direction of the first branch 2/joint section 31 connection, the seventh valve 47 being open in the direction of joint section 31/pressure sensor 34, opening the second, fourth, fifth and sixth valves 42, 44, 45, and 46, as well as the eighth valve 48, if any, and temporarily activating the pumping facility 32 to vacuum the first branch 2 and the joint section 31 of the fluid circuit;
(d) shutting-off the fourth and fifth valves 44 and 45 to isolate the pumping facility, and shutting-off the third and seventh valves 43 and 47;
(e) opening the first valve 41 to transfer into the first container 21 the liquid previously contained in capsule 1, and shutting-off again the first valve 41;
(f) waiting for a thermal balance between first container and the vapor trap 22 to establish, then opening the third valve 43 in the direction of first branch 2/joint section 31;
(g) waiting for the balance to establish, then measuring the pressure and the temperature in the joint section 31 and the variable volume enclosure 33 to deduce the amount of gas extracted therefrom;
(h) shutting-off the third valve 43;
(i) compressing the extracted gas to a predetermined pressure;
(j) vacuuming the gas recipient 39 and the portion of the joint section 31 between this recipient 39 and the third valve 43;
(k) opening the third valve 43 in the joint section 31/gas recipient 39 passage direction and emptying the variable volume enclosure 33 for passing the gas therein towards the gas recipient 39; and
(l) analyzing gas sent into the gas recipient 39.

Operation (c) is preferably carried out by vacuuming fluid circuit with a pressure at most equal to 0.001 mbar.

Operation (i) of compressing the extracted gas to a predetermined pressure is for example carried out by reducing the volume of the variable volume enclosure 33 and/or by opening the seventh valve 47 to communicate the pressurized inert gas bottle 38 with the joint section 31.

Advantageously, the process of the invention can also comprise at least a reiteration step itself including the operations of:

(m) shutting-off the third valve 43, opening the fourth, sixth and seventh valves 44, 46, and 47 in the direction of joint section 31/pressure sensor 34 and temporarily activating the pumping facility 32 to vacuum the joint section 31 of the fluid circuit;
(n) shutting-off the fourth and seventh valves 44 and 47 to isolate the pumping facility 32 from the joint section 31;
(o) repeating operation (f);
(p) repeating operation (g);
(q) repeating operation (h);
(r) repeating operation (i);
(s) repeating operation (j);
(t) repeating operation (k); and
(u) repeating operation (l).

The invention claimed is:

1. A facility for characterizing liquid-dissolved gas, this facility comprising at least a circuit of fluid including first and second branches, the first branch exhibiting a first end for the intake of the liquid and a second end being connected to the second branch, and each branch comprising at least a valve, wherein the first branch comprises, in series in this order between the first and second ends thereof, a first valve, a first container for collecting the liquid, a second valve designed to shut-off or establish a communication between the fluid input and said first container, and a vapor trap designed to trap a liquid vapor, wherein the second branch comprises a sealed joint section connected to the second end of the first branch, a third valve designed to shut-off or establish a communication between the first branch and the joint section, a pumping facility, a fourth valve designed to shut-off or establish a communication between the joint section and this pumping facility, a fifth valve designed to shut-off or establish a communication between the first branch and this pumping facility, said fifth valve being connected to the first branch between the first container and the vapor trap, a first variable volume enclosure, a sixth valve designed to shut-off or establish a communication between the joint section and said variable volume enclosure, measurement means connected at least selectively to the joint section and including at least a pressure sensor, a seventh valve making it possible to connect the joint section to the pressure sensor or to a pressurized inert gas bottle, and a liquid sampling capsule selectively connected to the first end of the first branch and whose said first valve controls the opening, in that the first container is temperature controlled and ultrasound emitting, and in that the measurement means comprise a temperature gauge.

2. The characterization facility according to claim 1 further comprising a gas recipient linked to the third valve and composed of a gas analyzer or a second variable volume enclosure for collecting extracted gas, said third valve being designed to shut-off or establish a communication between the joint section and said gas recipient.

3. The characterization facility according to claim 1, wherein the measurement means comprise at least a pressure sensor for measuring pressures at least equal to 1 mbar, and at least a pressure sensor for measuring pressures at most equal to 0.001 mbar.

4. The characterization facility according to claim 1, wherein the pumping facility comprises a primary pump and a turbo-molecular pump.

5. The characterization facility according to claim 1, wherein the capsule comprises a cylinder, a piston and a spring, the piston delimiting along with the cylinder a variable volume sealed room for containing the liquid, and the spring biasing the piston in a direction so as to reduce the volume of the room.

6. The characterization facility according to claim 1, wherein the first container is led to a temperature of 0 degrees Celsius, and wherein the vapor trap comprises a second container of which temperature is controlled at a value at most equal to −10 degrees Celsius.

7. A method for characterizing dissolved gas by implementing the facility according to claim 1, at a predetermined pressure, in a liquid, said method including at least an extracting step, and wherein the extracting step comprises at least the operations of:
  (a) collecting, at the predetermined pressure, a liquid sample in the sealed capsule having a known volume;
  (b) shutting off the first valve of the facility, connecting the capsule to the first end of the first branch;
  (c) opening the third valve of the facility in the direction of first branch/joint section connection, opening the seventh valve in the joint section/pressure sensor direction, opening the second, fourth, fifth and sixth valves, and temporarily activating the pumping facility to vacuum the first branch and the joint section of the fluid circuit;
  (d) shutting-off the fourth and fifth valves to isolate the pumping facility, and shutting-off the third and seventh valves;
  (e) opening the first valve to transfer into the first container the liquid previously contained in the capsule, and shutting-off again the first valve;
  (f) waiting for a thermal balance to establish between the first container and the vapor trap, then opening the third valve in the direction of first branch/joint section;
  (g) waiting for the balance to establish, then measuring the pressure and the temperature in the joint section and the variable volume enclosure to derive the amount of gas extracted therefrom.

8. The characterization method according to claim 7, wherein operation (c) is carried out by vacuuming the fluid circuit at a pressure at most equal to 0.001 mbar.

9. The characterization method according to claim 7, further comprising a step itself including the operations of:
  (h) shutting-off the third valve;
  (i) compressing the extracted gas to a predetermined pressure;
  (j) vacuuming the gas recipient and the portion of the joint section between this recipient and the third valve; and
  (k) opening the third valve in the direction of joint section/gas recipient passage and emptying the variable volume enclosure for passing the gas therein towards the gas recipient.

10. The characterization method according to claim 9, comprising an additional operation of analyzing gas sent in the gas recipient.

11. The characterization method according to claim 10, further comprising at least a reiteration step itself including the operations of:
  (m) shutting-off the third valve, opening the fourth, sixth valves and seventh valve in the direction joint section/pressure sensor and temporarily activating the pumping facility to vacuum the joint section of the fluid circuit;
  (n) shutting-off the fourth and seventh valve to isolate the pumping facility from the joint section;
  (o) repeating operation (f);
  (p) repeating operation (g);
  (q) repeating operation (h);
  (r) repeating operation (i);
  (s) repeating operation (j);
  (t) repeating operation (k); and
  (u) repeating operation (l).

12. The characterization method according to claim 9, wherein said operation (i) of compressing the extracted gas to a predetermined pressure is carried out by reducing the volume of the variable volume enclosure and/or by opening the seventh valve to communicate the pressurized inert gas bottle with the joint section.

13. The characterization method according to claim 9, wherein the liquid is substantially composed of water.

* * * * *